US006274879B1

(12) United States Patent
Best-Timmann

(10) Patent No.: US 6,274,879 B1

(45) Date of Patent: Aug. 14, 2001

(54) PROCESS AND DEVICE FOR THE QUANTITATIVE DETECTION OF A GIVEN GAS

(75) Inventor: Regina Best-Timmann, Lübeck (DE)

(73) Assignee: Dräger Medizintechnik GmbH, Lubeck (DE)

( * ) Notice: Subject to any disclaimer, the term of this patent is extended or adjusted under 35 U.S.C. 154(b) by 0 days.

(21) Appl. No.: 09/378,639

(22) Filed: Aug. 20, 1999

(30) Foreign Application Priority Data

Sep. 4, 1998 (DE) ........................................ 198 40 345

(51) Int. Cl.[7] ........................................ G01N 15/06

(52) U.S. Cl. ........................................ 250/573; 356/437

(58) Field of Search ........................................ 250/573, 574, 250/576, 222.2, 343, 341.8, 350; 356/437, 438, 440, 436; 340/632

(56) References Cited

U.S. PATENT DOCUMENTS 5,026,991 * 6/1991 Goldstein et al. .................. 250/343
5,448,071 9/1995 McCaul et al. ...................... 250/343
5,491,341 2/1996 McCaul et al. ...................... 250/343

OTHER PUBLICATIONS

M. Kroll et al., Nov. 2, 1987, Measurement of gaseous oxygen using diode laser spectroscopy, Appl. Phys. Lett. 51 (18), © 1987 American Institute of Physics.

N. Husson et al., Jun. 30, 1992, Management and Study of Spectroscopic Information: The Geisa Program, J. Quant. Spectrosc. Radiat. Transfer vol. 48, No. 5/6 pp. 509–518, Jun. 1992.

* cited by examiner

*Primary Examiner*—Que T. Le
(74) *Attorney, Agent, or Firm*—McGlew and Tuttle, P.C.

(57) ABSTRACT

In a process for the quantitative detection of a given gas and in a device for the quantitative detection of a given gas, a gas sample (3), which may contain the given gas as a component, is irradiated with a diode laser (1) operating in a single mode and free of mode jumps, the wavelength of which being continuously tuned by varying the laser control current. The laser control current is varied by superimposing a sinus modulation current of a predetermined frequency to a periodically varied d.c. component so that a laser wavelength range is scanned in the area of the absorption line of the given gas. The intensity of the laser radiation after passing through the gas sample is measured by means of a detector. The d.c. component of the detector signal and the second harmonic of the detector signal corresponding to the doubled frequency of the sinus modulation current are determined. The concentration of the given gas is calculated by means of the detector signals in a control and evaluating device, wherein the line width of the absorption line, which is included in the calculation and depends on the unknown composition of the gas sample, is determined on the basis of the minimum and maximum of the second harmonic, which are measured during the variation of the d.c. component of the laser control current.

25 Claims, 2 Drawing Sheets

PROCESS AND DEVICE FOR THE QUANTITATIVE DETECTION OF A GIVEN GAS

FIELD OF THE INVENTION

The present invention pertains to a process and a device for the quantitative detection of a given gas.

BACKGROUND OF THE INVENTION

Such a gas analysis method and such a gas analyzer operate with laser spectroscopy, preferably based on infrared absorption, wherein a component of a gas sample is analyzed by the use of special methods for laser triggering and evaluation of the measured signals in order to find out whether this component, i.e., the given gas, is contained as a component in the gas sample and if so, at what concentration. The optical analyzer typically contains one or more lasers as radiation sources, optical elements for guiding the beam, as well as a sample cell and one or more radiation detectors.

A prior-art process for laser control and signal evaluation, as described, e.g., by M. Kroll et al. in Appl. Phys. Lett., Vol. 51 (18), pp. 1465–1467 ("Measurement of gaseous oxygen using diode laser spectroscopy"), pertains to the gas spectroscopic measurement of oxygen concentrations on the basis of the radiation absorption in the wavelength range of 760 nm to 770 nm (near infrared). The laser diode with a monitor diode type ML 440S from the manufacturer Mitsubishi, which is used as the radiation source there, is supplied with a control current that is composed of a d.c. component and an a.c. component with a frequency of 5 kHz. The working point of the laser diode is set with the d.c. component of the control current, while the a.c. component brings about a periodic sweeping in the range of the absorption lines. To achieve a possibly harmonics-free control of the laser diode, a sinus curve is selected for the alternating current. The laser diode and the monitor diode are mounted as a block on a thermostat-controlled surface, wherein the laser diode is brought to one of the known absorption lines of oxygen by varying the temperature of this surface.

After having passed through the gas sample, the radiation emitted by the laser diode reaches a detector means, which is connected to an evaluating circuit. The evaluating circuit consists essentially of a lock-in amplifier, with a signal input to which the measured signal of the detector means is supplied, and a reference input to which a signal voltage of the doubled a.c. component frequency of the laser diode is fed.

The evaluating circuit also contains a differential amplifier, which is likewise connected to the measured signal of the detector means and which receives a signal of the monitor diode, which signal is proportional to the radiation output from the laser diode. The output voltage of the differential amplifier corresponds to the absorption of the measured oxygen concentration. Since the absorption line is particularly weak in the case of oxygen, this so-called second harmonic of the absorption line, which corresponds to the output voltage of the lock-in amplifier, is used for the concentration measurement. The advantage of this process is that due to the detection with the doubled a.c. component frequency of the laser diode, the measuring frequency is shifted into a range in which the laser noise is markedly reduced. Furthermore, the great offset is eliminated, so that the dynamic range can be made more efficient for the evaluation.

A process for the laser spectroscopic determination of oxygen concentrations on the basis of a direct absorption measurement in the wavelength range of 760 nm to 770 nm has been known from U.S. Pat. No. 5,448,071. The laser diode with a model ML-4405 monitor diode from Mitsubishi, which is likewise used as the radiation source, is supplied with direct current varying in steps and having a periodic curve, wherein each period consists of a series of intervals with constant current. In one embodiment, the duration of each interval with constant current is about 0.1 msec to 10 msec. A phase-sensitive detection, as was described above, is not possible.

In this process, the base line is determined in a first step several line widths from the center of the absorption line by detecting the measuring radiation having passed through the gas sample, on the one hand, and a reference radiation, which does not pass through the gas sample, on the other hand. The base line thus determined is subtracted from the absorption signal of the line center, which is measured in a subsequent step. The base line drift, noise and/or interference effects can be eliminated by adjusting additional control circuits, so that the output signal corresponds only to a change in the signal in the gas sample and is thus proportional to the concentration.

Furthermore, to determine the center of the absorption line, the control current and thus the frequency of the laser are set and varied stepwise in such a way that the laser is led to a point of the ascending flank of the absorption line, to the center, and to a point of the descending flank of the absorption line, wherein the difference between the center and the point of the ascending flank is equal to the difference between the center and the point of the descending flank, i.e., the current intervals are equal. Should the mean current value not exactly correspond to the center of the line, the two points to the right and left of the center show different absorption signals. The control current will then be adjusted until the two signals to the right and left of the center become equal.

Based on this process, the points of the ascending and descending flanks are selected according to U.S. Pat. No. 5,491,341 such that their absorption signals correspond to half the absorption signal of the line center. The current intervals are then a measure of the width of the absorption line. Changes in the line width, as they occur, e.g., in the case of a change in the composition of the gas sample, can be compensated with this information.

One drawback of both the process described by M. Kroll et al. and the process according to U.S. Pat. No. 5,448,071 is that the use of the Fabry-Perot Laser diode ML-4405 does not permit long-term stable use, because mode jumps usually occur due to aging processes after an operating time of one year and the working point will no longer be located on the selected absorption line. Then, correct measurements are no longer possible. Tuning to another absorption line is not easily possible, because a stable mode must be found. Furthermore, the sensor must be recalibrated.

Furthermore, a great drawback of the process described by M. Kroll et al. is the fact that it is not possible to compensate changes in the line width of the absorption lines, which are caused by temperature and pressure variations as well as by collisions with different components of a gas sample (foreign gas effect), which lead to a distortion of the concentration measurement.

SUMMARY AND OBJECTS OF THE INVENTION

The primary object of the present invention is to provide a process and a device for the quantitative detection of a given gas, especially for medical use, which operate fast, with high resolution and have long-term stability, and in which environmental effects, such as temperature, pressure, and especially foreign gas effects are compensated without external information on the composition of the gas sample to be analyzed.

According to the invention, a process for the quantitative detection of a given gas is provided. The process includes irradiating a gas sample, which sample may contain the given gas as a component, with a single mode diode laser operating free of mode jumps, whose wavelength can be varied continuously by varying the laser control current. The laser control current is varied by a sinus modulation current of a predetermined frequency being superimposed to a d.c. component being slowly varied periodically, so that a laser wavelength range in the area of an absorption line of the given gas is scanned through. The intensity of the laser radiation which passed through the gas sample is measured by means of a detector and determination of the d.c. component of the detector signal and of the second harmonic of the detector signal corresponding to the doubled frequency of the sinus modulation current. The concentration of the given gas is calculated on the basis of the detector signals, wherein the line width of the absorption line involved in the calculation, which depends on the unknown composition of the gas sample, is determined on the basis of the minimum and maximum of the second harmonic, which are measured during the variation of the d.c. component of the laser control current.

According to the invention a device for the quantitative detection of a given gas is also provided. The device includes a single mode diode laser operating free of mode jumps, the wavelength of which can be continuously varied by varying the laser control current. A device for varying the laser control current is provided which is adapted to supply a laser control current which controls the laser to scan through a wavelength range in the area of an absorption line of the given gas, the control current consisting of a d.c. component which is slowly periodically varied and to which a sinus modulation current of a predetermined frequency is superimposed. A detector is provided for measuring the intensity of the laser radiation which passed through a gas sample (which may contain the given gas as a component). A device is provided for determining the d.c. component of the detector signal and the second harmonic of the detector signal corresponding to the doubled frequency of the sinus modulation current. A control and evaluating device is provided, which is designed to calculate the concentration of the given gas on the basis of the detector signals and to determine the line width of the absorption line, which is involved in the calculation and which depends on the unknown composition of the gas sample, on the basis of the minimum and maximum of the second harmonic, which are measured during the variation of the d.c. component of the laser control current.

In accordance with the present invention a single mode diode laser operating free of mode jumps, whose wavelength can be varied continuously at a given temperature by varying the laser control current, is used as the radiation source for the absorption spectroscopy performed. An especially suitable laser diode is a VCSEL ("Vertical Cavity Surface Emitting Laser"), as for example the model LA-SEN-OXS manufactured by VIXEL Corporation, U.S.A.

While it is relatively simple to compensate the effect of the temperature and pressure of the gas sample on the measurement results for the concentration of the given gas, the line width of the absorption line must also be known to determine an accurate measurement result in the case of varying composition of the gas sample. Since the line width strongly depends on the composition of the gas sample, which in principle is unknown, it cannot be directly calculated. While a direct measurement of the line width is performed in the process according to U.S. Pat. No. 5,448,071 described in the introduction, the line width is determined in the present invention on the basis of the minimum and maximum of the second harmonic, which are measured during the variation of the d.c. component of the laser control current.

Consequently, it is possible to compensate the effects of temperature, and pressure variations as well as foreign gas effects on the measurement results in the present process and device for the quantitative detection of a given gas, and it is also possible, e.g., to eliminate contamination effects and variations in the output power of the diode laser. The concentration of the given gas can be determined with a relative accuracy in the percent range.

In a preferred embodiment, the given gas is oxygen. In this case, the present invention provides an optical oxygen sensor, which is especially well suited for use in environments in which a fast and accurate oxygen measurement with high resolution and with long-term stability is required. This applies, e.g., to medical applications, e.g., the monitoring of patients during anesthesia. The oxygen concentration can be determined with the optical oxygen sensor, resolved for individual breaths, at a relative accuracy of about 2% of the measured value. It is particularly advantageous that the line width is determined in the process, so that the sensor can be used at a great variety of gas compositions, temperatures and pressures. In the case of applications in anesthesia, varying components are usually present in the patient gas, and the influences of these gases on the results are completely taken into account in the process according to the present invention, so that the sensor ensures high accuracy and resolution.

Other fields of use of the process according to the present invention and of the device according to the present invention for the quantitative detection of a given gas are, e.g., in diving and safety technology. The process and the device of the invention may be used, in principle, for any given gas that is to be detected and whose concentration, if that gas is present, is to be measured, by suitably tuning to an absorption line to be analyzed or even to a plurality of absorption lines to be analyzed, which are preferably in the infrared range. It is also contemplated to use a device that can be used for a plurality of different gases by switching over to preselected absorption ranges.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

The process according to the present invention and the device according to the present invention will be described below based on the example of oxygen, which is to be quantitatively detected as the given gas. An absorption line of oxygen is analyzed in a range around 760 nm. However, as was mentioned above, the present invention may be used for other gases and at other absorption wavelengths as well.

Figure 1:
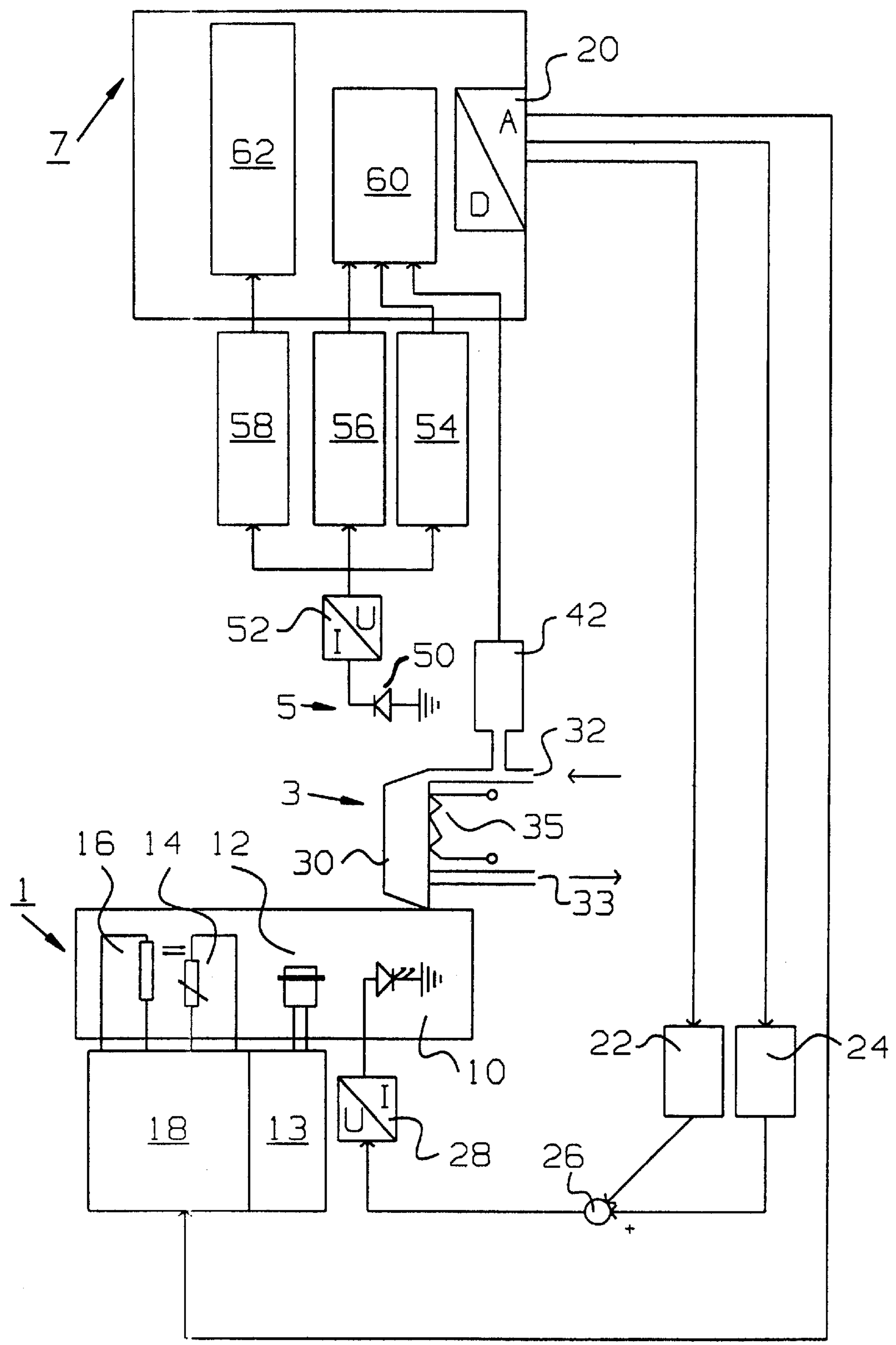
FIG. 1 is a schematic view of a device according to the present invention for the quantitative detection of a given gas.

FIG. 1 shows a schematic view of an optical gas sensor, which is a device for the quantitative detection of a given gas. The process for the quantitative detection of a given gas can be carried out by means of such a device.

The essential components of the device are a laser module 1 with an associated electronic unit and having a laser diode 10 as the radiation source, a sample chamber 3 for a gas sample to be analyzed, in which the given gas may be present as one component, a detector 5 with an associated electronic unit for detecting the absorption signals, and a control and evaluating device 7.

The laser module 1 contains a laser diode 10, namely a model LA-SEN-OXS VCSEL from the manufacturer VIXEL Corporation, U.S.A., in the exemplary embodiment. This laser diode 10 can operate in a single mode free of mode jumps, and its wavelength can be varied continuously by varying the laser control current.

The laser module 1 also contains a piezo drive 12, which is connected to a control and regulating device 13. The piezo drive 12 provides for a longitudinal vibration of the laser diode 10 along the axis of the optical system at an amplitude of $\lambda/4$ and greater of the wavelength of the absorption line to be analyzed in order to reduce interferences that occur in the system due to the use of laser radiation.

The temperature of the laser diode 10 is detected by means of a temperature sensor 14 (NTC) and is adjusted to the selected operating temperature by means of a Peltier element 16 in order to permit the stable operation of the laser diode 10. The temperature sensor 14 and the Peltier element 16 are connected to a temperature control and regulating device 18.

A focusing lens for the laser diode 10 is also integrated within the laser module 1.

The wavelength of the laser diode 10 can be varied continuously at the predetermined temperature of the laser diode 10 by varying the laser control current. If a model LA-SEN-OXS laser diode is used, the range of variation around 760 nm is about 1 nm. The laser control current consists of a d.c. component, which is set at a laser wavelength in the vicinity of an absorption line, and a harmonic modulation current which has a predetermined frequency and which is superimposed to the d.c. component. The modulation current is a sinus current in the exemplary embodiment and has a frequency of about 4.7 kHz, and its modulation amplitude causes a change in the wavelength that corresponds to about 2.3 times the line width of the absorption line. A low-frequency (about 100 Hz) saw-tooth current is superimposed to the d.c. component of the laser control current, so that a selected absorption line of the gas to be analyzed is swept periodically.

To supply the laser diode 10 with a laser control current that is variable over time, a unit 22 for generating a variable d.c. voltage and a sinus generator 24 for generating a sinus voltage of about 4.7 kHz are controlled by a signal from a digital-analog converter 20, which is contained in the control and evaluating device 7. The output voltages of the unit 22 and of the sinus generator 24 are added in an adder 26. The output of the adder 26 is connected to a voltage-current converter 28, at which output the laser control current, which is variable over time, is present.

Figure 2:
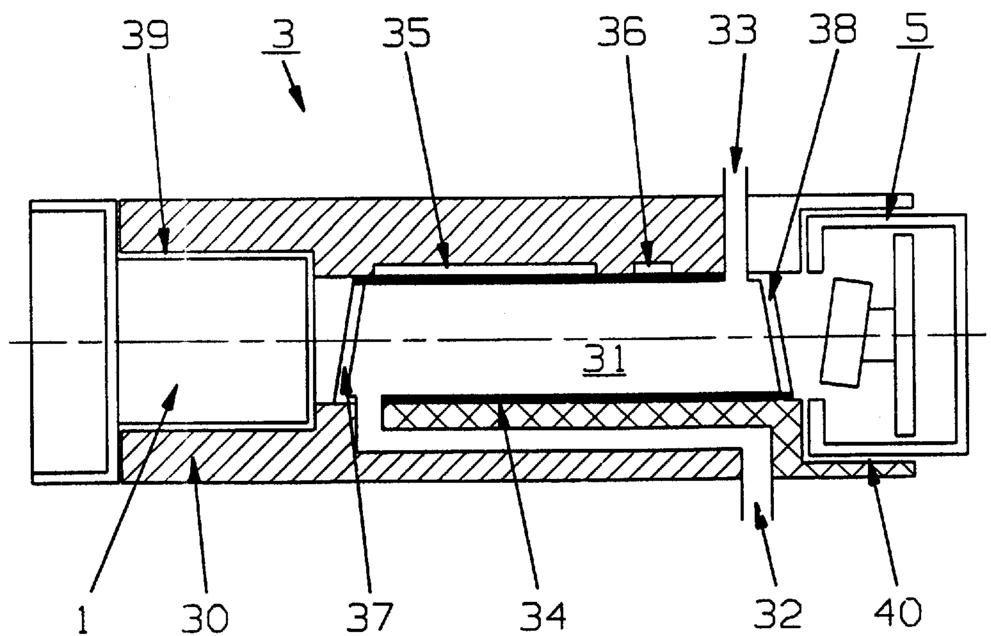
FIG. 2 is a longitudinal sectional view through the sample cell used in the device according to FIG. 1.

The radiation emitted by the laser diode 10 falls on the gas sample, which is located in the sample chamber 3. FIG. 2 shows an enlarged view of the sample chamber 3. The essential component is a housing 30, which is designed as a sample cell and can be easily removed from the device. This is advantageous, e.g., when the optical gas sensor is used to monitor the oxygen for a patient under anesthesia, so that the inside of the housing 30 comes into contact with the patient gas and may become contaminated as a result.

The gas sample to be analyzed is present in an inner chamber 31 of the housing 30, through which the gas sample flows continuously. The gas is drawn into the inner chamber 31 via a gas inlet 32 and is discharged via a gas outlet 33. The gas passing through the inner chamber 31 is preheated in the area of the gas inlet by means of a heated sample cell jacket 34, so that it has a temperature exceeding 40° C. in the inner chamber 31 in order to prevent the condensation of water on the windows and walls of the inner chamber 31. The temperature of the sample cell is regulated and maintained at a constant value by means of a heater 35 and a temperature sensor 36. The temperature sensor 36 measures the temperature of the housing 30, which approximately corresponds to the gas temperature.

A first, tilted optical window 37 and a second, tilted optical window 38 are located on the front sides of the inner chamber 31. The laser module 1 is inserted into a recess 39, which is located in front of the first window 37, while the detector 5 is arranged in a recess 40 in front of the second window 38. The radiation emitted from the laser module 1 is focused on the detector 5 through the first window 37, the inner chamber 31 and the second window 38. The tilt of the optical components, such as the first window 37, the second window 38, the detector 5 and the lens contained in the laser module 1, ensure a further reduction of the interferences occurring during the measurements.

A pressure sensor 42, which measures the pressure in the inner chamber 31, is mounted in front of the gas inlet 32 (see FIG. 1).

The detector 5 used is a photodiode 50, see FIG. 1, whose current signal is converted into a voltage signal by means of a current-voltage converter 52. This detector signal is split into a d.c. component (more precisely a direct-voltage component), which is subsequently amplified in an amplifier 54 and filtered, and a component (so-called second harmonic) which results from demodulation in a lock-in amplifier 56 with twice the modulation frequency of the sinus modulation current, which components are subjected to further processing. Because of the weak absorption of oxygen, the d.c. component of the detector signal is essentially proportional to the laser output and also reflects an attenuation of the laser radiation due to contamination in the sample chamber 3. The maximum of the second harmonic is proportional to the concentration of the gas being measured. A device 58 may be used to detect the third harmonic, which can be useful for finding the maximum and the minimum of the second harmonic.

The control and evaluating device 7 has a block 60 for calculating the concentration of the given gas and a block 62 for finding the minimum and the maximum of the second harmonic. The representation of the control and evaluating device 7 in FIG. 1 is very schematic. In practice, the control and evaluating device 7 contains a microprocessor, interfaces for the incoming signals and the processed signals and for the outgoing commands, as well as an input and output unit. How the concentration of the given gas is calculated on the basis of the detector signals will be described below in detail on the basis of the theoretical principles.

The arrangement described in the exemplary embodiment has the following advantages: Due to the use of the model LASEN-OXS VCSELs 10, which can be varied continuously and has a single mode emission in the working range selected (1.2 times the threshold current to 1.8 times the threshold current), it is possible to provide a sensor that has long-term stability. This laser diode 10 can always be tuned to the same absorption line, because no mode jumps occur. Aging processes in the laser, which lead to a reduction in the laser output, play a minor role only. The broad range of about 1 nm, in which continuous tuning is possible by means of the laser control current, makes it possible to select an intense absorption line with a good signal-to-noise ratio. Because of the high tuning rate of about 0.24 nm/mA, only small modulation amplitudes are needed. A nonlinear characteristic in the laser output as a function of the control current plays a less important role than in the case of conventional Fabry-Perot lasers with low tuning rates of about 0.02 nm/mA or less.

Furthermore, the modular design of the device with replaceable sample cell 30 makes it possible to replace the sample cell 30 on the spot in the case of contamination of the sample cell, e.g., with mucus or water drops, without additional adjustment or without the need for calibration at the factory. This reduces the costs of ownership for the user.

How the concentration of the given gas can be calculated at high accuracy on the basis of the detector signals will be described below. The theoretical principles will be described first.

A laser beam of the intensity Io, which passes through an absorbing medium having the gas density N and an absorption coefficient k over a path L, is attenuated exponentially according to the Bouguer-Lambert-Beer law according to Equation (1):

$$I=I_0 \exp(-N\cdot k\cdot L)=I_0(1-N\cdot k\cdot L) \tag{1}$$

in which, for weak absorptions as in the case of oxygen, the exponent can be expanded in a series. In the case of a pressure-broadened Lorentz profile, the absorption coefficient k is described by $$k=\frac{S}{\pi\cdot\alpha}\cdot\frac{1}{((\nu-\nu_0)/\alpha)^2+1} \tag{2}$$

wherein S is the line intensity, $\alpha$ the line width (HWHM), $\nu$ the laser frequency $\nu$ and $\nu_0$ the frequency at the center of the absorption line.

As was described above, the laser control current and thus the laser frequency $\nu$ are modulated according to Equation (3):

$$\nu=\nu_{av}+a\cos\omega t \tag{3}$$

in which $\nu_{av}$ is the average laser frequency, a is the modulation amplitude of the variation in the laser frequency as a consequence of the sinus modulation current, and $\omega$ is the angular frequency of the sinus modulation current. $\nu_{av}$ is not constant over time, but is changed slowly by the periodically varied d.c. component of the laser control current with a characteristic time that is large compared with $1/\omega$, but it may be considered to be constant over time compared with the rapid sinus modulation.

The right-hand factor of the absorption coefficient k according to Equation (2) can be expanded into a Fourier series according to L. C. Philippe and R. K. Hanson, Applied Optics, Vol. 32, pp. 6090–6103 (1993)

$$[((\nu-\nu_0)/\alpha)^2+1]^{-1}=\Sigma H_n(\nu_{av},a)\cdot\cos n\omega t \tag{4}$$

Ignoring other terms, such as $H_1$ and $H_3$, which is permissible in the case of the use of the VCSEL model LA-SEN-OXS because of the low modulation amplitude, and introducing the dimensionless parameters $m=a/\alpha$ and $x=(\nu_{av}-\nu_0)/\alpha$ according to J. Reid and D. Labrie, Appl. Phys. B, Vol. 26, pp. 203–210 (1981), in which x is the detuning of the laser from the line center, the following equation is obtained for the detector signal $S_2$, which is called the second harmonic:

$$Q_2=\frac{S_2}{I_{0av}}=\frac{S\cdot N\cdot L}{\pi\cdot\alpha}\cdot H_2(x,m) \tag{6}$$

as it is obtained from Equation (1), Equation (2) and Equation (4). The second harmonic is normalized here to the average intensity $I_{0av}$ (d.c. component of the detector signal).

The line intensity S as well as the gas density N and the line width $\alpha$ are temperature-dependent; N and $\alpha$ 5also depend on the pressure, and $\alpha$ additionally depends on the composition of the gas mixture in the gas sample (foreign gas effect).

The gas density N can be calculated from the partial pressure $p_a$ or the concentration C of the gas to be detected by means of the ideal gas equation:

$$N(p,T)=p_a(k_B\cdot T)=C\cdot p/(k_B\cdot T) \tag{7}$$

Here, $k_B$ is the Boltzmann constant, T is the (absolute) temperature of the gas sample, and p is the pressure of the gas sample measured by the pressure sensor 42.

According to the document "The GEISA Data Bank 1991 Version, N. Husson, B. Bonnet, N. A. Scott, A. Chedin, Gestion et Etude des Informations Spectroscopiques Atmospheriques [Management and Study of Atmospheric Spectroscopic Information], Laboratoire de Meteorologie Dynamique du CNRS, Ecole Polytechnique, 91128 Palaiseau Cedex, France", the line intensity $S_i$ of the ith rotational line can be expressed as:

$$S_i(T)=S_i(T_G)\cdot(T_G/T)\cdot\exp[-h\cdot c(E_i/k_B)\cdot(1/T-1/T_G)] \tag{8}$$

in which $T_G$ is the reference temperature, T is the measuring temperature, h is Planck's quantum of action, and c is the velocity of light; the ground state energy of the ith rotational line $E_i$ is expressed in wave numbers in Equation (7).

The dependence of the result sought for the concentration C on the temperature T and the pressure p can be easily compensated by measurements of T and p. The foreign gas effect which causes a change in the line width $\alpha$ cannot be ignored because it broadens the line of oxygen by up to 20%, depending on the gas composition, e.g., in the case of medical use. A correction by calculation requires either the exact knowledge of the gas composition and corresponding correction algorithms or the knowledge of the line width $\alpha$. According to the present invention the foreign gas effects are compensated independently from external information on the composition of the gas sample, namely by the indirect determination of the line width $\alpha$. A direct measurement of $\alpha$ is possible in direct absorption spectroscopy only, but not if the second harmonic is measured.

The line width $\alpha$ is determined indirectly according to the present invention. To do so, it is necessary to know the minimum and the maximum of $Q_2$, i.e., of the second harmonic, normalized for the particular d.c. component of the detector signal. As can be seen in Equation (6), $H_2(x,m)$ changes during the variation of $\nu_{av}$ so that $Q_2$ reaches a maximum $Q_{2max}$ and a minimum $Q_{2min}$. Refering to the quotient $Q_{2max}/Q_{2min}$ as R, the following equation is obtained from Equation (6):

$$R(m)=Q_{2max}/Q_{2min}\approx H_2(\max,m)/H_2(\min,m) \tag{9}$$

Figure 3:
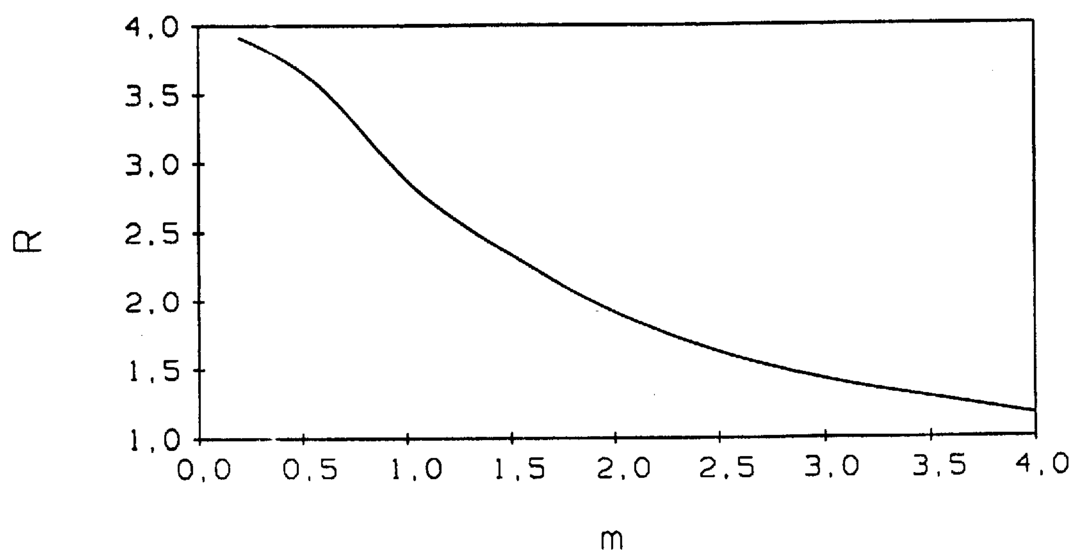
FIG. 3 is a graphic representation of the function R(m) used to determine the line width.

Here, "max" denotes the value at x=0 at which $H_2(x,m)$ with the value of m being fixed assumes its maximum, and "min" correspondingly denotes the value of x at which the minimum is assumed. As was shown by J. Reid and D. Labrie, Appl. Phys. B, Vol. 26, pp. 203–210 (1981), R(m) is an unambiguous function of $m=a/\alpha$. This means that a value of m can be unambiguously assigned to each measured value of R, see FIG. 3. Since the modulation amplitude a is predetermined and thus known, $\alpha$ can thus be determined.

For the calibration of the gas sensor with a reference gas sample that contains the given gas at a known concentration $C_{ref}$, reference values $T_{ref}$ for the temperature, $p_{ref}$ for the pressure, $\alpha_{ref}$ for the line width and reference values of the second harmonic of the detector signal and for the d.c. component of the detector signal are recorded. By now forming the quotient $Q_2/Q_{2ref}$ and introducing the gas density N according to Equation (7) and the line intensity according to Equation (8), the following equation is obtained from Equation (6):

$$Q_2 = Q_{2ref} C\cdot\alpha_{ref}\cdot p\cdot T_{ref}^2\cdot\frac{H_2(\max,m)}{C_{ref}\cdot\alpha\cdot p_{ref}\cdot T^2\cdot H_2(\max,m_{ref})}\cdot(1/s) \tag{10}$$

in which $$(1/s)=\exp[-h\cdot c\cdot(E_i/k_B)\cdot(1/T-1/T_{ref})] \tag{11}$$

For Equation (10) it is assumed that the maxima $Q_2$ and $Q_{2ref\ max}$ measured during the variation of the d.c. component of the laser control current are used for $Q_2$ and $Q_{2ref}$ respectively, and the values $H_2(\max,m)$ and $H_2(\max,m_{ref})$ corresponding to these d.c. components are used for $H_2(m)$ and $H_2(m_{ref})$, respectively. This has an advantageous effect on the measurement error; however, it is also possible, in principle, to use measured values for the second harmonic of the detector signal at another point in time during the periodic variation of the d.c. component of the laser control current if the corresponding value of the parameter x is used for the second Fourier component.

When the temperature of the gas sample is regulated and $T=T_{ref}$, the factor (1/s) according to Equation (11) (approximately) corresponds to the value 1 and is thus negligible. By solving for the concentration C being sought, $$C = C_{ref}\cdot\frac{Q_2\cdot\alpha\cdot p_{ref}\cdot T^2\cdot H_2(\max,m_{ref})}{Q_{2ref}\cdot\alpha_{ref}\cdot p\cdot T_{ref}^2\cdot H_2(\max,m)}\cdot s \tag{12}$$

is then obtained, in which s=1.

The operation of the device explained in connection with FIG. 1 for determining the concentration of the given gas (oxygen in the exemplary embodiment) will be described below. The process is preferably controlled automatically by the control and evaluating device 7, and the calculations necessary for the evaluation also take place in the control and evaluating device 7.

The laser control current is varied by the sinus modulation current being superimposed to the periodically varied d.c. component so that the laser wavelength is periodically scanning over a selected absorption line of oxygen. During the scanning the d.c. component of the detector signal and the second harmonic of the detector signal, as well as the temperature T and the pressure p of the gas sample are detected. A base line (background) of the second harmonic, which is subtracted from the measured values obtained for the second harmonic in the area of the absorption line, is obtained from the measured values obtained for the second harmonic outside the absorption line. Thus, background-corrected values are used for the second harmonic, because the background does not disappear completely due to a slight nonlinearity of the VCSEL. The relevant data for the determination of the concentration C being sought are obtained by normalizing the corresponding background-corrected value for the second harmonic, $S_2$, to $I_{0av}$ according to Equation (6). The corresponding d.c. component of the detector signal can be used for the value of $I_{0av}$.

The maximum $Q_{2max}$ and the minimum $Q_{2min}$ are now determined from the measured curve thus obtained for $Q_2$, and the ratio R is determined from this according to Equation (9). (There are two minima $Q_{2min}$, from which the mean value can be calculated for use in Equation (9).) The variable m is determined from R by means of FIG. 3 (or a table of values stored in the control and evaluation unit 7) and the line width $\alpha$ is thus determined according to Equation (5). With m being known the second Fourier component $H_2(\max,m)$ can also be calculated.

If these measurements and calculations are performed on the one hand for the gas sample to be analyzed, but on the other hand also for a reference gas sample (see above), all the variables needed for use of Equation (12) are determined, so that the oxygen concentration being sought can be calculated by means of Equation (12). By this way of evaluation foreign gas effects and the effect of the temperature T and of the pressure p on the result for C are compensated.

To set up the gas sensor for operation for subsequent measurements, an coarse current scan is performed for the laser diode 10 (or, if the laser module has a plurality of laser diodes, for all laser diodes). The modulated laser control current is now scanned through from the threshold current over the entire range in which the laser operates in a single mode up to about twice the threshold current value. For example with air as the test gas, it is thus possible to detect up to six oxygen lines. If the maximum of one absorption line exceeds a defined threshold value, the line is analyzed more finely by means of a fine scan and the shape of the curve is checked. The values for $Q_{2max}$ and the noise N are determined at a line free of interference or noise. The normalized signal-to-noise ratio ($Q_{2max}/N$) is used for the assessment. The line with the highest normalized signal-to-noise ratio is selected as the measuring line, and the corresponding temperature/laser control current combination of the laser is defined as the working point and stored.

The signal originating from the oxygen contained in the air outside the gas sample is taken into account as a background signal (offset) in the evaluation. (Such air is enclosed mainly between the laser module 1 and the first window 37 as well as between the second window 38 and the detector 5, see FIG. 2). Fine scans are repeatedly performed over this absorption line during the subsequent calibration, the offset-corrected measured values are averaged and the measuring parameters are determined from them.

Thereafter, the regular measuring operation can be performed, i.e., as was described in detail above: Fine scan over the absorption line and measurement of $S_2$ (second harmonic of the detector signal), $I_{0av}$ (d.c. component of the detector signal), p (pressure of the gas sample), and T (temperature of the gas sample), determination of $Q_{2min}$ and $Q_{2max}$, determination of R and m as well as $\alpha$, and, finally, calculation of the oxygen concentration C.

The procedure for setting up the gas sensor for operation may be performed at the factory, but also by the user, especially if the control and evaluating device 7 is provided with a calibration program intended for this purpose.

With model LA-SEN-OXS VCSELs, a laser wavelength range of about 1 nm can be continuously scanned by means of the laser control current. As a result, a plurality of absorption lines of a given gas can be detected in one scan. The lines can be identified by comparing the theoretical ratio of the line intensities from the above-mentioned GEISA document with the measured ones.

According to Equation (6), the ratio of the standardized second harmonic of two absorption lines i and n equals $$\frac{Q_{2i}}{Q_{2n}} = \frac{S_i}{S_n} \cdot \frac{\alpha_n}{\alpha_i} \cdot \frac{H_2(\max, m_i)}{H_2(\max, m_n)} \approx \frac{S_i}{S_n} \tag{13}$$

If there are a plurality of lines, a clear pattern is obtained from the ratios, which greatly facilitates the identification of the lines.

One advantage of known absorption lines is that the exponential factor (1/s) can be calculated from Equation (11) if the ground state energy $E_i$ is known (e.g., from the GEISA document) and measured values for T and $T_{ref}$ are available. No complicated temperature control of the sample chamber 30, which would guarantee $T=T_{ref}$, so that the exponential factor can be set at one, is necessary in this case. This aspect is of particular interest for applications in the case of oxygen measurements outside medicine.

While specific embodiments of the invention have been shown and described in detail to illustrate the application of the principles of the invention, it will be understood that the invention may be embodied otherwise without departing from such principles.

What is claimed is:

1. A process for the quantitative detection of a given gas, the process comprising:

irradiating a gas sample, which may contain the given gas as a component, with a single mode diode laser operating free of mode jumps, whose wavelength can be tuned continuously by varying the laser control current;

varying the laser control current by a sinus modulation current of a predetermined frequency superimposed to a d.c. component which is slowly varied periodically, so that a laser wavelength range in the area of an absorption line of the given gas is scanned;

measuring the intensity of the laser radiation after passing through the gas sample by means of a detector and determining the d.c. component of the detector signal and the second harmonic of the detector signal corresponding to the doubled frequency of the sinus modulation current; and calculating the concentration of the given gas on the basis of the detector signals, wherein the line width of the absorption line involved in the calculation, which depends on the unknown composition of the gas sample, is determined on the basis of the minimum and maximum of the second harmonic, which are measured during the tuning of the d.c. component of the laser control current.

2. The process in accordance with claim 1, wherein a VCSEL ("Vertical Cavity Surface Emitting Laser") is used as the laser diode.

3. The process in accordance with claim 1, wherein the second harmonic of the detector signal is determined by means of a lock-in amplifier.

4. The process in accordance with claim 1, wherein a background-corrected value, which is determined by subtracting a background value of the second harmonic, which background value is measured outside the absorption line, is used as the particular value for the second harmonic.

5. The process in accordance with claim 1, wherein to determine the line width $\alpha$, the quotient $Q_{2max}/Q_{2min}$ of the maximum of the normalized second harmonic to the minimum of the normalized second harmonic is formed, wherein the second harmonic is normalized to the corresponding d.c. component of the detector signal, and wherein $Q_{2max}/Q_{2min}=R(m)$ is an unambiguous function of the ratio $m=a/\alpha$ of the known modulation amplitude a of the variation in the laser frequency occurring as a consequence of the sinus modulation current to the line width $\alpha$.

6. The process in accordance with claim 1, wherein the concentration C of the given gas in the gas sample is calculated according to the equation $$C = C_{ref} \cdot \frac{Q_2 \cdot \alpha \cdot P_{ref} \cdot T^2 \cdot H_2(x, m_{ref})}{Q_{2ref} \cdot \alpha_{ref} \cdot p \cdot T_{ref}^2 \cdot H_2(x, m)} \cdot s$$

in which $Q_2$ is the second harmonic normalized to the d.c. component of the detector signal, a is the line width determined, p is the measured or known pressure of the gas sample, T is the measured or known temperature of the gas sample, $H_2(x,m)$ is the second Fourier component of the Fourier expansion of $$[((\nu_{av}+a \cos \omega t-\nu_0)/\alpha)^2+1]^{-1}=[(x+m \cos \omega t)^2+1]^{-1}$$

in which $\nu_{av}$ is the laser frequency component based on the variable d.c. component of the laser control current, a is the modulation amplitude of the laser wavelength variation due to the sinus modulation current, $\omega$ is the angular frequency of the modulation current, $\nu_0$ is the frequency in the center of the absorption line, $x=(\nu_{av}-\nu_0)/\alpha$ is the parameter of the detuning of the laser from the center of the line, and m is the quotient $a/\alpha$, which depends on the current value of the d.c. component, and s is a temperature-dependent factor that depends on the energy levels of the given gas, and wherein the subscript ref refers to the corresponding values of a reference gas sample with known concentration $C_{ref}$.

7. The process in accordance with claim 6, wherein for calculating C, the maxima $Q_{2max}$ and $Q_{2ref\ max}$, which are determined during the variation of the d.c. component of the laser control current, are used for $Q_2$ and $Q_{2ref}$, respectively, as well as the values $H_2(\max,m)$ and $H_2(\max,m_{ref})$ corresponding to the same d.c. components, are used for $H_2(x,m)$ and $H_2(x,m_{ref})$, respectively.

8. The process in accordance with claim 6, wherein the temperature T of the gas sample is measured and regulated and that the factor is set at s=1.

9. The process in accordance with claim 6, wherein the factor s is calculated according to the formula $$s=\exp[h\cdot c\cdot(E_i/k_B)\cdot(1/T-1/T_{ref})]$$

in which $E_i$ is the ground state energy of the absorption line (in wave numbers), T is the measured or known temperature of the gas sample, $T_{ref}$ is the measured or known temperature of the reference gas sample, h is Planck's quantum of action, c is the velocity of light, and $k_B$ is the Boltzmann constant.

10. The process in accordance with claim 1, wherein measurements are performed at two or more absorption lines of the given gas, and that the ratios of the respective second harmonics is used to identify the lines.

11. The process in accordance with claim 1, wherein the given gas is oxygen.

12. The process in accordance with claim 11, wherein the signal originating from the oxygen contained in the air outside the gas sample is taken into account as a background signal.

13. A device for the quantitative detection of a given gas, the device comprising:

a diode laser operating in a single mode and free of mode jumps whose wavelength can be continuously tuned by varying the laser control current;

a device for varying the laser control current which device is adapted to achieve scanning of a wavelength range in the area of an absorption line of the given gas by a periodically slowly varied d.c. component of the control current to which a sinus modulation current of a predetermined frequency is superimposed;

a detector for measuring the intensity of the laser radiation after passing through a gas sample which may contain the given gas as a component;

devices for determining the d.c. component of the detector signal and the second harmonic of the detector signal corresponding to the doubled frequency of the sinus modulation current; and a control and evaluating device for calculating the concentration of the given gas on the basis of the detector signals and for determining the line width of the absorption line, which line width is involved in the calculation and depends on the unknown composition of the gas sample, on the basis of the minimum and maximum of the second harmonic, which are measured during the tuning of the d.c. component of the laser control current.

14. The device in accordance with claim 13, wherein said laser diode is part of a diode laser module and is a "Vertical Cavity Surface Emitting Laser".

15. The device in accordance with claim 13, wherein said device for determining the second harmonic of the detector signal has at least one lock-in amplifier.

16. The device in accordance with claim 13, wherein said control and evaluating device is designed to use as the particular value for the second harmonic a background-corrected value, which is determined by subtracting a background value of the second harmonic measured outside the absorption line.

17. The device in accordance with claim 13, wherein said control and evaluating device is adapted to form the quotient $Q_{2max}/Q_{2min}$ of the maximum of the normalized second harmonic to the minimum of the normalized second harmonic, wherein the second harmonic is normalized to the particular d.c. component of the detector signal, and wherein $Q_{2max}/Q_{2min}=R(m)$ is an unambiguous function of the ratio $m=a/\alpha$ of the known modulation amplitude a of the variation in the laser frequency resulting from the sinus modulation current to the line width $\alpha$.

18. The device in accordance with claim 13, wherein said control and evaluating device is adapted to calculate the concentration C of the given gas in the gas sample according to the equation $$C = C_{ref}\cdot\frac{Q_2\cdot\alpha\cdot p_{ref}\cdot T^2\cdot H_2(m_{ref})}{Q_{2ref}\cdot\alpha_{ref}\cdot p\cdot T_{ref}^2\cdot H_2(m)}\cdot s$$

in which $Q_2$ is the second harmonic normalized to the d.c. component of the detector signal, $\alpha$ is the determined line width, p is the measured or known pressure of the gas sample, T is the measured or known temperature of the gas sample, $H_2(x,m)$ is the second Fourier component of the Fourier expansion of $$[(\nu_{av}+a\cos\omega t-\nu_0)/\alpha)^2+1]^{-1},$$

in which $\nu_{av}$ is the laser frequency component based on the variable d.c. component of the laser control current, a is the modulation amplitude of the variation in the laser wavelength due to the sinus modulation current, $\omega$ is the angular frequency of the modulation current, $\nu_0$ is the frequency in the center of the absorption line, $x=(\nu_{av}-\nu_0)/\alpha$ is the parameter of the detuning of the laser from the center of the line, and m is the quotient $a/\alpha$, which depends on the current value of the d.c. component, and s is a temperature-dependent factor that depends on the energy level of the given gas, and wherein the subscript ref refers to the corresponding values of a reference gas sample with known concentration $C_{ref}$.

19. The device in accordance with claim 18, wherein said control and evaluating device is adapted to use the maxima $Q_{2max}$ and $Q_{2ref\,max}$ measured during the variation of the d.c. component of the laser control current for $Q_2$ and $Q_{2ref}$, respectively, as well as the values $H_2(\max,m)$ and $H_2(\max, m_{ref})$ corresponding to these d.c. components for $H_2(x,m)$ and $H_2(x,m_{ref})$ for the calculation of C.

20. The device in accordance with claim 18, wherein a temperature sensor for measuring and a regulating device for regulating the temperature T of the gas sample are provided, and that the factor is set at s=1.

21. The device in accordance with claim 18, wherein said control and evaluating device is designed to calculate the factor s according to the equation $$s=\exp[h\cdot c\cdot(E_i/k_B)\cdot(1/T-1/T_{ref})]$$

in which $E_i$ is the ground state energy of the absorption line (in wave numbers), T is the measured or known temperature of the gas sample, $T_{ref}$ is the measured or known temperature of the reference gas sample, h is Planck's quantum of action, c is the velocity of light, and $k_B$ is the Boltzmann constant.

22. The device in accordance with claim 13, wherein said control and evaluating device is designed to perform measurements at two or more absorption lines of the given gas and to use the ratios of the respective two harmonics to identify the lines.

23. The device in accordance with claim 13, wherein the given gas is oxygen.

24. The device in accordance with claim 23, wherein said control and evaluating device is designed to take into account the signal originating from the oxygen contained in the air outside the gas sample as a background signal.

25. The device in accordance with claim 13, wherein said sample chamber for receiving the gas sample, has a said window each on two opposite sides, which window is transparent to the radiation emitted by said diode laser.

* * * * *